United States Patent [19]
Myler et al.

[11] Patent Number: 5,941,895
[45] Date of Patent: *Aug. 24, 1999

[54] CARDIOVASCULAR STENT AND RETRIEVAL APPARATUS

[75] Inventors: Richard Myler, Hillsborough; Julius G. Hammerslag, San Juan Capistrano, both of Calif.

[73] Assignee: Hemodynamics, Inc., San Clemente, Calif.

[ * ] Notice: This patent is subject to a terminal disclaimer.

[21] Appl. No.: 09/009,813

[22] Filed: Jan. 21, 1998

Related U.S. Application Data

[63] Continuation of application No. 08/707,524, Sep. 4, 1996, Pat. No. 5,733,302.

[51] Int. Cl.$^6$ ..................................................... A61M 29/00
[52] U.S. Cl. ........................................... 606/195; 606/198
[58] Field of Search ..................................... 606/108, 195, 606/198, 191, 205, 206

[56] References Cited

U.S. PATENT DOCUMENTS

| | | |
|---|---|---|
| 4,655,771 | 4/1987 | Wallsten . |
| 4,733,665 | 3/1988 | Palmaz . |
| 4,740,207 | 4/1988 | Kreamer . |
| 4,762,128 | 8/1988 | Rosenbluth . |
| 4,776,337 | 10/1988 | Palmaz . |
| 4,830,003 | 5/1989 | Wolff et al. . |
| 4,922,905 | 5/1990 | Strecker . |
| 5,007,926 | 4/1991 | Derbyshire . |
| 5,078,726 | 1/1992 | Kreamer . |
| 5,092,877 | 3/1992 | Pinchuk . |
| 5,116,318 | 5/1992 | Hillstead . |
| 5,122,154 | 6/1992 | Rhodes . |
| 5,123,917 | 6/1992 | Lee . |
| 5,147,370 | 9/1992 | McNamara et al. . |
| 5,147,385 | 9/1992 | Beck . |
| 5,163,952 | 11/1992 | Froix . |
| 5,192,297 | 3/1993 | Hull . |
| 5,649,906 | 7/1997 | Gory et al. ................. 606/108 |
| 5,785,715 | 7/1998 | Schatz ....................... 606/108 |

FOREIGN PATENT DOCUMENTS

| | | |
|---|---|---|
| 0 364 420 | 4/1990 | European Pat. Off. . |
| 0 393 788 | 10/1990 | European Pat. Off. . |
| 0 466 412 | 1/1992 | European Pat. Off. . |

*Primary Examiner*—Michael Buiz
*Assistant Examiner*—Kevin Truong
*Attorney, Agent, or Firm*—Knobbe, Martens, Olson & Bear, LLP

[57] ABSTRACT

Disclosed is a removable cardiovascular stent, an apparatus for the retrieval of the stent and a method for removal of the stent. The removable stent includes radially inwardly extending engagement members for contacting an extraction catheter. The extraction catheter includes a tubular body and an axially moveable guidewire, each adapted to grasp the engagement members of the tubular stent. The stent is elongated in an axial direction thereby reducing the cross-sectional area of the stent. The stent can be removed directly, or can fit within the tubular body of the extraction catheter for atraumatic removal from the treatment location.

12 Claims, 5 Drawing Sheets

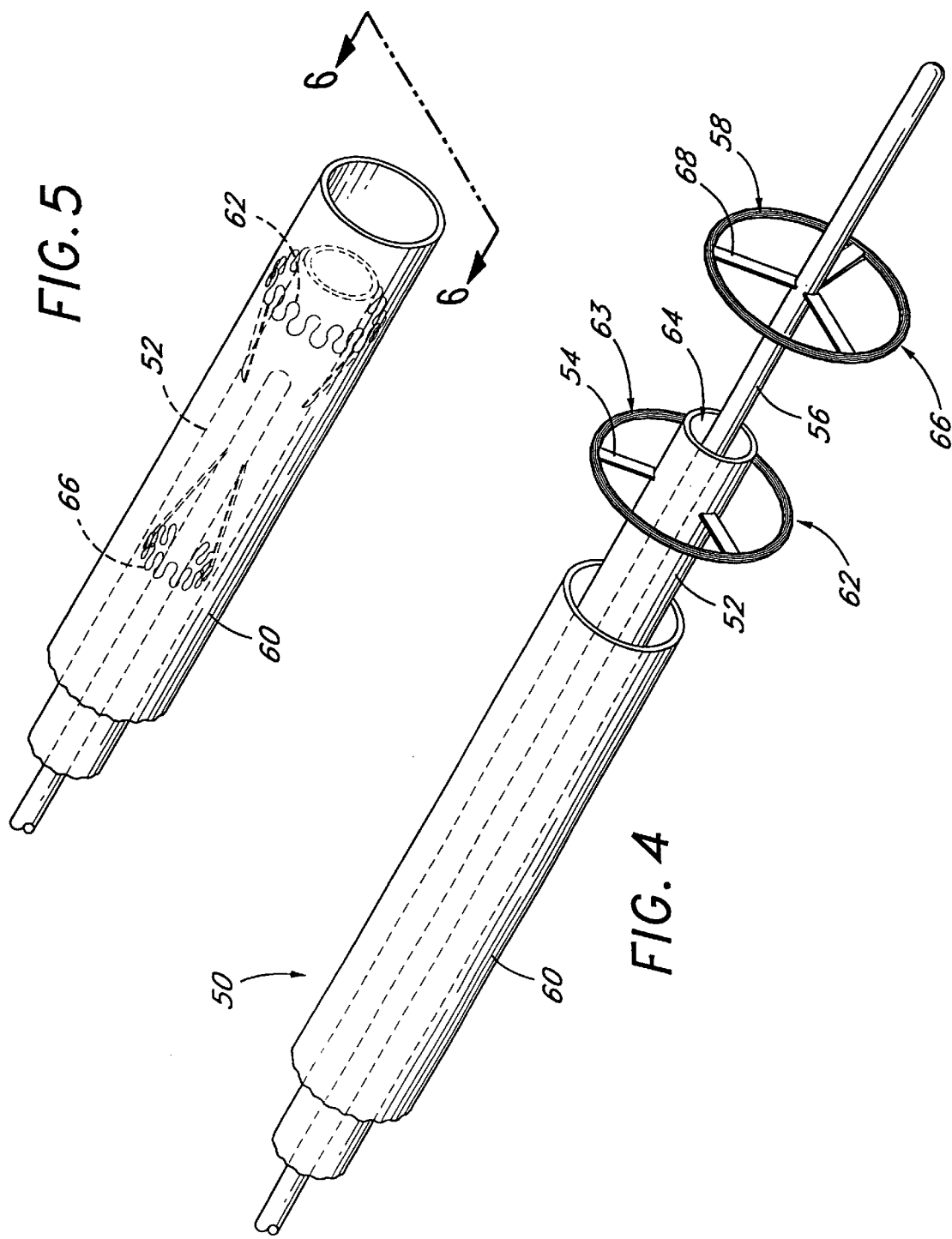

CARDIOVASCULAR STENT AND RETRIEVAL APPARATUS

This application is a continuation of prior application Ser. No. 08/707,524 filed Sep. 4, 1996 now abandoned.

BACKGROUND OF THE INVENTION

The present invention relates to cardiovascular stents which can be inserted into a body lumen. More particularly, the present invention relates to a removable cardiovascular stent designed to operate with an extraction catheter to enable easy retrieval of the implanted stent.

The implantation of a stent to maintain patency of a body lumen is well known in the art. A stent is typically a tubular metallic or polymeric body, which is carried on a dilatation catheter to a specific vascular location. In one cardiovascular application, a stent is mounted on a balloon catheter and positioned at the appropriate site within an artery. The balloon is dilated to expand the stent against the vascular wall. The balloon is thereafter deflated and removed, leaving the expanded stent in place in the artery. The stent may also be self or thermally expanding, thus, not requiring a balloon for placement. Due to the structural integrity of the stent, the arterial wall is supported by the stent and prevented from recollapsing.

One shortcoming of conventional stents is that most stents are not designed to facilitate removal following implantation. In an increasing number of instances, it has become desirable to remove a stent after implantation. Although some procedures have been developed to remove a stent from a vascular location, these methods typically. require complex instrumentation, or expose the luminal intima to undesirable levels of trauma.

For example, European Patent Application No. 0 364 420 discloses a device for transluminal implantation or extraction. The disclosed device is a removal catheter which includes an expandable jaw. The removal catheter is threaded into the body and positioned proximally of the stent. Next, the expandable jaws are pushed out of the catheter into an expanded distal position. The jaws are maneuvered along the vascular wall and are positioned to engage the exterior surface of the stent. Once the jaws engage the stent, pressure is applied to the exterior surface of the stent by contracting the jaws to force the stent to compress to a diameter small enough to fit within the removal catheter. Once the stent is compressed, the jaws are pulled back into the catheter body with the stent contained within the jaws.

One disadvantage of this extraction technique and other similar techniques is that the extraction tool, i.e., the expandable jaws, must press against the vascular wall in order to engage and compress the stent. By pressing against the vascular wall with the extraction tool, there is an increased risk of further traumatizing the treatment site. In addition, by externally compressing the stent with the jaws there is an increased risk of deforming the stent in a manner which would result in the protrusion of the stent in between the individual components of the jaws. The protruding portion of the deformed stent could potentially damage the artery upon removal of the stent.

Thus, there remains a need for an improved cardiovascular stent specially adapted for radial expansion and contraction. In addition, there remains a need for a stent manipulation device to implant and/or remove a stent with minimal trauma to the vascular wall.

SUMMARY OF THE INVENTION

In accordance with one aspect of the present invention, there is provided a removable implantable cardiovascular stent. The stent comprises a tubular body having a proximal and distal end and central lumen extending therethrough. The wall of the tubular body may be solid such as latex or a synthetic polymer; microporous; or in the form of a lattice such as a wire mesh having a plurality of openings therethrough. The stent is configured to permit radial expansion, such as under the force generated by balloon dilatation, and radial contraction in response to axial elongation. Alternatively, the stent is radially expandable by axial compression. As a further alternative, the stent is self expanding such as through the memory of a resilient material or thermally activated memory metal.

At least two radially inwardly extending engagement members are provided on the tubular body. Preferably, at least one engagement member is provided at each of the proximal and distal ends thereof. The engagement members are adapted to engage an extraction catheter, for axial elongation of the stent.

In a preferred embodiment, the stent is partially or completely enclosed in a smooth, polymeric layer for inhibiting adhesion between the stent and the vascular wall. The layer may be in the form of an envelope which completely isolates the stent from contact with either the vascular wall or the blood stream. In one embodiment, at least the radially outward most surface of the layer is permeable to medication for drug delivery directly to the vascular wall. Permeability may be achieved by providing a plurality of perforations in the outer layer. Preferably, the envelope comprises an elastic material such as latex.

In accordance with a further aspect of the present invention, there is provided an extraction catheter for removing an implanted removable cardiovascular stent of the present invention. The extraction catheter comprises an elongate tubular body having a proximal control end and a distal functional end. At least one lumen extends from the proximal control end to the distal functional end.

The extraction catheter is provided with a proximal engagement member for engaging a first end of the stent, and a distal engagement member for engaging a second end of the stent. A control is provided at the proximal end of the catheter, for advancing the distal engagement member and the proximal engagement member axially apart from each other. In a preferred embodiment, the extraction catheter further comprises an outer tubular sheath, for receiving the extraction catheter and elongated stent following radial reduction at a vascular site.

In accordance with further aspects of the present invention, there are also provided a method of removing a cardiovascular stent, and a method of treating a preselected site in a body lumen. These methods generally comprise the steps of positioning a reversibly expandable stent at the preselected site, and radially enlarging the stent from a first reduced diameter to a second enlarged diameter. The stent is thereafter axially elongated to reduce its crosssectional area, and transluminally removed from the patient.

These and other features and advantages of the present invention will become apparent from the detailed description of preferred embodiments which follows, when considered together with the attached drawings and claims.

BRIEF DESCRIPTION OF THE DRAWINGS

FIG. 4 is a partial perspective view of an embodiment of the extraction catheter of the present invention having two expandable extraction halos in an expanded position.

FIG. 5 is a partial perspective view of the embodiment of the extraction catheter illustrated in FIG. 4 with the expandable extraction halos in the retracted position.

DETAILED DESCRIPTION OF PREFERRED EMBODIMENTS

Figure 1:
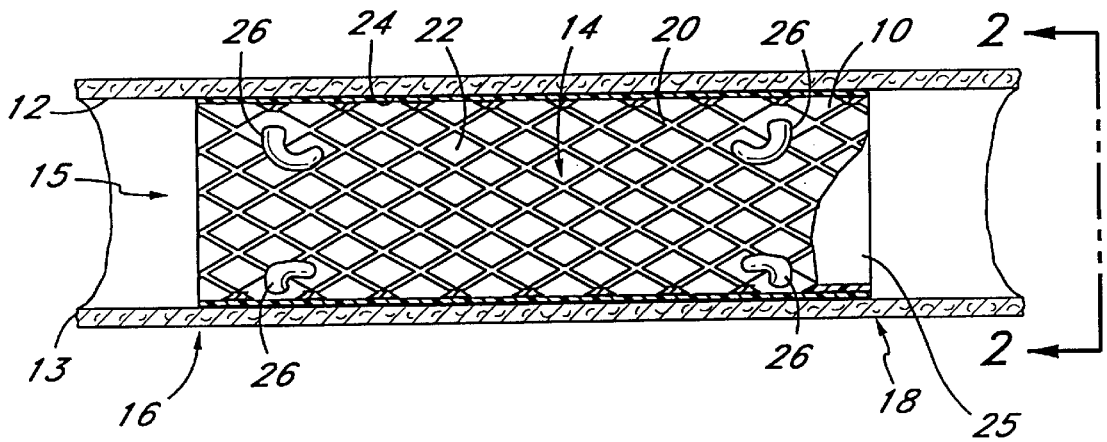
FIG. 1 is a cross sectional view of an embodiment of the stent of the present invention positioned within a body lumen.

Referring to FIG. 1, there is disclosed a representation of a radially expandable and compressible stent 10. Stent 10 is illustrated in its expanded position at a treatment location adjacent vascular wall 12 in an artery 13, in accordance with one aspect of the present invention. Stent 10 comprises a generally tubular body 14 with a central lumen 15 extending between proximal end 16 and distal end 18. Although the stents and catheters are described herein in the context of cardiovascular applications, they are readily useable in any body lumen or hollow organ as will be appreciated by one of skill in the art.

The stent 10 can be balloon expandable, self expanding, thermally expandable or expandable by other means and still incorporate the inventions described herein. Metal mesh or woven walled stents are well suited for expansion on a dilatation catheter, as discussed infra. Alternatively, tubular stents formed from flexible non-metal materials such as elastomeric polymers or rubber (latex) can also be radially reduced by axial elongation in accordance with the present invention. Polymeric stents can be provided with relatively fluid impenetrable walls, or porous walls such as to allow drug delivery, as will be apparent to one of skill in the art.

In the illustrated embodiment, stent 10 has a lattice structure 20 with a plurality of openings 22 therethrough. This design facilitates radial expansion of tubular stent 10 from a first insertion diameter to a second expanded diameter, and radial reduction by elongating the tubular stent 10 along its longitudinal axis.

Preferably, the lattice comprises a braided or woven wire mesh. For example, mesh woven from 0.005 inch diameter stainless steel or other deformably (mallable) material, such as gold wire in a weave pattern much like the outer conductor of coaxial electrical cable may be used. Alternatively, a lattice pattern can be stamped or cut from flat sheet stock and rolled and soldered or brazed to produce an unexpanded stent. As will be apparent to one skilled in the art, a variety of lattice patterns can be devised which meet the functional criteria described herein. Therefore, the illustrated lattice structure 20 should be considered exemplary only.

Preferably, stent 10 is made of a design and/or material which is sufficiently strong to maintain the expanded diameter of the stent 10 against compressive forces exerted by the vascular wall 12. At the same time, the material should be sufficiently malleable or loosely woven to reversibly expand and contract between the insertion diameter and the desired expanded diameter.

A number of materials have sufficient strength and malleability to form the mesh-like lattice structure 20 of the stent 10, i.e., some common metals, alloys, composite materials and plastics. Stent 10 is preferably also made from materials which have at least a biocompatible exterior surface. Most preferably, the stent comprises a homogeneous material throughout, such as stainless steel or gold. Use of a radiopaque material or marker facilitates proper placement and removal.

Biocompatibility can be enhanced by applying any of a variety of coatings to the surfaces 24 of the stent 10. The processes for applying a biocompatible coating are known in the art. In addition, other coatings, such as to promote or inhibit tissue ingrowth or inhibit thrombus formation, can also be applied as will be understood by one of skill in the art.

Figure 2:
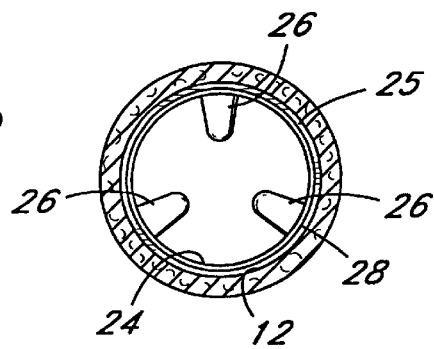
FIG. 2 is an end view of the embodiment of the stent of the present invention positioned within a body lumen as in FIG. 1.

In a preferred embodiment, the interior and exterior walls of stent 10 are enclosed in a thin polymeric envelope 25. The interior portion of polymeric envelope 25 is illustrated in cut away fashion in FIG. 1 and is deleted from the remaining Figures for clarity. The exterior portion of envelope 25 is illustrated in FIGS. 1 and 2.

Suitable envelope materials include elastic materials such as latex and others that can be readily selected by one of skill in the art. Polyethylene or PET or other envelopes with or without an outer silicone or PTFE coating can be preformed with ridges or indentations on the interior surface to accommodate the projections 26. In general, biocompatible materials which can tolerate expansion of the stent between the insertion diameter and expanded diameter can be used.

The envelope may be produced, for example, by inserting the stent into a preformed tubular envelope having one open end and sealing the envelope closed, or other techniques within the skill in the art. One such envelope can be readily formed by inserting a first end of a tubular sleeve back inside of the tube and advancing it through the tube to the second end of the tubular sleeve. After insertion of the stent, the open end of the envelope can be sealed in any of a variety of ways known in the art.

The exterior surface of the envelope which will contact the arterial wall is optionally made porous to enable the release of drugs from the envelope and/or stent 10 to the treatment site. Advantageously, the stent permits drug delivery directly to a preselected site in a body lumen. The envelope can act as a reservoir and be filled with a medication prior to implantation at the desired treatment location. Preferably, the drugs are released when the stent 10 is expanded to its implanted diameter. During the expansion of the stent 10, the diameter of the pores of the envelope are expanded and pressure is applied to the mediation enabling the drug to escape into the vascular wall 12. Alternatively, the stent can be provided with a solid drug carrier such as an impregnated porous solid wall or sponge for timed drug delivery.

In a non-drug delivery embodiment, the polymeric cover on stent 10 can similarly take the form of an enclosed envelope such as a tube within a tube which is heat sealed, solvent bonded or otherwise secured at each end. Alternatively, a tubular sheath surrounding only the outer circumference of stent 109 will also accomplish the adhesion inhibition discussed infra. The tubular sheath can be made from an elastic material such as latex, which will expand with the stent, or of a relatively inelastic material such as PET or other conventional balloon material which is preformed in the size of the implanted (expanded) stent. In general, any of a variety of materials or configurations of an outer sheath or envelope which will provide an adhesion inhibiting layer between the stent and the vascular wall is desired. Preferably, the polymeric cover additionally covers the inner wall of the stent to also minimize flow turbulence or thrombus formation sites.

Angioplasty, whether performed by balloon, lasers or atherectomy devices creates a wound in the enlarged arterial wall. When a wound is created in the body, healing action starts immediately and may continue for a week or more. The healing action includes thrombi, cell formation and scar tissue.

One purpose of the temporary stent 10 is to modify the healing response to prevent re-occlusion of the artery (restenosis).

One problem of bare open meshed stents is that the healing reaction penetrates the interstices of the mesh, making the removal, even with the relatively atraumatic method disclosed herein, inherently harmful to the intima, even after a short stay.

The provision of a smooth polymeric cover or envelope around the mesh is, in part, to prevent thrombus and scar cell formations from penetrating the interstices of the mesh, which would cause trauma upon removal of the stent 10. Use of the smooth cover disclosed herein promotes formation of a thin film covering the arterial wound and adhering as little as possible to the stent.

For the above reasons, even the expanded pores for drug delivery should be small enough to minimize or prevent cell penetration, but large enough for drug delivery. Fortunately, liquid drug molecules are usually much smaller than cells, potentially by as much as 1:1000. Preferably, the stent is longer than the treated wound, thus preventing healing cells from moving around the end edges of the stent.

The wall thickness of the stent 10 may vary depending on the required application. The wall thickness of the stent 10 should be sufficient when the stent 10 is in its expanded configuration to withstand radially inwardly directed force exerted by the vascular wall 12. However, the wall should be sufficiently thin for a selected construction material to enable the stent 10 to be expanded by a conventional balloon catheter and contracted by an extraction catheter of the present invention. In addition, the stent should exert sufficient pressure against the arterial wall to minimize or prevent migration away from the treatment site. The optimal balance of wire diameter and tightness of the weave can be determined through routine experimentation by one of skill in the art.

Typically, the wall thickness of the stent 10 will be no more than about 0.015 inches and no less than about 0.005 inches for a woven wire stent made from stainless steel and having an unexpanded diameter of about 0.030 inches. In some cases a wall thickness less than about 0.005 inches may be desired. In addition, some instances may require a wall thickness of greater than about 0.015 inches, but may be difficult to radially contract for extraction.

The wall thickness will generally be substantially uniform throughout the axial length of the stent 10, particularly in the case of woven wire stents. However, the wall thickness on the medial portion of the stent 10 may be different from the wall thickness at the proximal and/or distal ends 16, 18 of the stent 10, such as in the case of stamped or rolled stents, to affect the inflated configuration or strength profile of the stent.

The insertion diameter and axial length of the stent 10 will vary with the specific intended application. One skilled in the art will be readily able to choose the appropriate insertion diameter of the stent 10 depending on the diameter of the artery 13 to be treated and the maximum expandable diameter of the stent 10. The location of the treatment site and the desired percentage of restored flow will influence the necessary expansion characteristics of the stent.

A typical stent 10 is able to expand to at least about 300% of its insertion diameter and preferably, to as much as 400% or more of its insertion diameter. Optimally, the clinician will choose a stent such that the stent 10 will be expanded to an implanted diameter which is between about 200% and 500% of the insertion diameter. The implanted diameter will typically approximate the native diameter in the absence of the stenosis, which is on the order of about 2.5 mm to about 3.5 mm in the coronary artery. Peripheral arteries generally have a native interior diameter within the range of from about 3 mm to about 10 mm (iliac) with the femoral at about 6 mm.

Further, the clinician will select a stent 10 having an axial length that will sufficiently support the treatment site on the vascular wall 12. The axial length of the stent 10 for coronary artery applications will typically be in the range from about 1 cm to about 3 cm. In peripheral vascular applications, stent lengths within the range of from about 1 cm to about 5 cm are to be expected in most cases, although the length may vary considerably from case to case depending upon the anatomy and the underlying etiology at the treatment site. It may also be desired to implant two or more short stents end to end such as in a remote stenosis which may be difficult to reach with a longer stent due to its relatively low bendability, or to permit continued perfusion through a branch artery exiting between two adjacent stents.

The stent 10 of the present invention includes at least a proximal (FIG. 3) and in another embodiment also a distal (FIG. 1) engagement member spaced axially apart along the length thereof. The engagement members can assume any of a variety of physical configurations, so long as they enable the removal catheter to accomplish an axial elongation of the implanted stent. Preferably, the engagement members are elastically deformable radially outwardly, or otherwise provided with smooth surfaces so that they will not puncture a dilatation balloon.

One example of a shape of the engagement members of the present invention is a hook like shape as illustrated in FIG. 1. However, other applicable shapes of the engagement members may be chosen by one skilled in the art. For example, any of a variety of rigid or moveable radially inwardly biased ramp structures can also readily be used. Extensions of integral wire segments in a woven wire stent can also be used as will be apparent to one of skill in the art.

Engagement members, such as projections 26, are secured to the lattice structure 20 of the stent 10 with sufficient structural integrity to enable a sufficient axially extending force to be applied to the engagement members to stretch the length of the stent 10 without causing the engagement members to disengage from the stent 10. Engagement members, such as projections 26, may be integrally formed with the lattice structure 20, or they may be secured to the lattice using attachment techniques known in the art, such as brazing, soldering, solvent bonding, spot welding, or others, as appropriate for the construction material of the stent.

In the embodiment of the stent 10 illustrated in FIG. 1, the opposing sets of engagement members comprise one or more inwardly extending projections 26 at each axial end thereof. Preferably, two to five or more inwardly extending projections 26 are positioned on each end of stent 10. The projections 26 are generally radially symmetrically positioned about the circumference of the stent. See FIG. 2. However, alternative positioning of the projections 26 are possible as will be recognized by one skilled in the art.

More than one projection 26 at each end are generally desired. Greater than about five projections 26 per end may also be used. However, much more than about three or four projections 26 may undesirably interfere with the effective flow area of the arterial lumen or produce undesirable turbulence in the blood flow.

In the embodiment shown in FIG. 1, each of the proximal and distal ends 16, 18 of the stent 10 has the identical number of radially inwardly extending projections 26. However, in some cases, it may be advantageous for the proximal and distal ends 16, 18 of the stent 10 to have a different number of projections 26 in order accommodate particular embodiments of the removal catheter.

Figure 3:
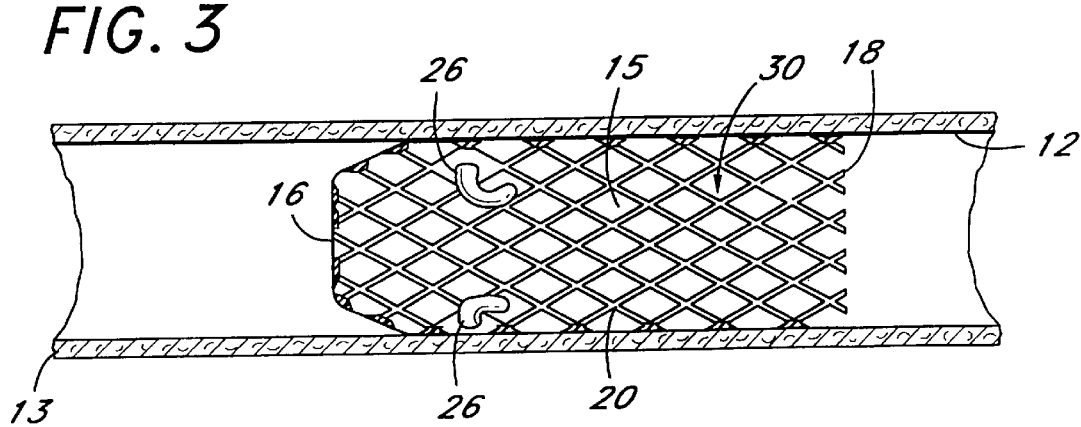
FIG. 3 is a cross sectional view of another embodiment of the stent of the present invention positioned within a body lumen.

FIG. 3 illustrates an alternative embodiment of the cardiovascular stent 30, implanted against the vascular wall 12 of an artery 13. Radially inwardly extending projections 26 are only provided on the proximal end 16 of the stent 30. In the present context, "proximal" and "distal" shall be determined with reference to the removal catheter, and not necessarily to the arterial anatomy.

The cardiovascular stent 30 has a generally tubular body as described above. However, the stent 30 is seated on the dilatation balloon such that the proximal end 16 of the stent 30 extends proximally beyond the proximal end of the balloon. When the balloon is inflated, the proximal end 16 of the stent 30 is not fully expanded, thus resulting in the smaller diameter at proximal end 16 as illustrated in FIG. 3. Alternative means for providing a reduced proximal diameter can also be used, such as providing a stent with a nonexpandable proximal section, greater wall thickness, or others that can readily be devised by one of skill in the art.

In this embodiment, the proximal end of the tubular stent has a sufficiently reduced diameter that it inclines radially inwardly away from the vascular wall. The diameter of the installed stent at its most proximal end is sufficiently small that it will fit within the central lumen of a tubular catheter, such as will be described infra. In one embodiment, the distal end of the central lumen of the removal catheter is flared radially outwardly to more easily receive the stent as will be appreciated by one of skill in the art.

Removal of the stent is accomplished by engaging the proximal end of the stent within the removal catheter and grasping the projections 26 as will be discussed. Projections 26 are pulled axially in the proximal direction, causing a radial reduction in the size of the stent at the point the stent enters the smaller diameter of the lumen in the tubular extraction catheter. The extraction catheter is preferably gradually advanced distally over the entire length of the stent so that the stent is forced to a reduced diameter to fit within the catheter. The catheter and stent can then be removed from the vascular site.

A second aspect of the present invention comprises an extraction catheter 50 for use with the cardiovascular stent 10 of the present invention. See FIGS. 4–7. The catheter 50 preferably includes an elongate tubular body 52 having a contact surface 54 for contacting the proximal engagement structure on the stent. A moveable member such as a guidewire 56 is provided with an opposing contact surface 58 for contacting the distal engagement members of the stent 10. When the guidewire 56 travels in an axial direction away from the tubular body 52, the stretching force applied to the stent 10 will cause the stent 10 to become elongated, and simultaneously reduced in diameter for removal. Optionally, an outer tubular body 60 is also provided to assist in both the placement of the catheter, and atraumatic removal of the contracted stent.

Referring to FIGS. 4–7, the contact surface 54 on one embodiment of the extraction catheter 50 is provided on the proximal surface of an engagement structure such as a radially outwardly extending annular ring or halo 62 for engaging the proximal engagement members of the stent 10. Halo 62 is preferably supported by one or more spokes 63 which may be similar to spokes 68 discussed infra.

Any of a variety of alternative support structures for supporting a contact surface 54, such as an annular flange, plurality of radial spokes or others can be used as will be apparent to one of skill in the art. For example, the halo 62 or a radial flange can extend less than the entire circumference of the catheter. Alternatively, a plurality of discrete structures such as ramps which incline radially outwardly in the proximal direction and are resiliently deflectable can provide a useful ratchet like locking structure.

In general, the annular halo 62 or flange is preferred because of manufacturing convenience and because it does not require any particular rotational alignment. In the annular flange embodiment, the flange is preferably deflectable in the proximal direction yet sufficiently resistant to distal pressure to permit insertion into the stent and also accomplish the desired result as will become apparent. The halo 62 or flange is preferably formed from a high tensile strength, soft and easily bondable material such as nylon. Additional construction parameter are discussed infra. The annular halo 62 can extend from about 0.010 inches to about 0.050 inches or greater beyond the outer radius of the tubular body 52, depending upon the diameter of the intended artery and diameter of the catheter.

An elongate central lumen 64 extends throughout the tubular body 52 for axially movably receiving an extraction guidewire 56. The extraction guidewire 56 generally comprises a flexible central rod or spring coil provided with a second annular halo 66 suspended from the guidewire 56 by a series of spokes 68. The guidewire 56 may comprise any of a variety of guidewires known in the art. Most preferably, guidewire 56 comprises a steerable guidewire such as any of those disclosed in U.S. Pat. No. 5,108,368 to Hammerslag et al. and entitled "Steerable Medical Device", the disclosure of which is incorporated herein by reference.

The annular halo 66 and spokes 68 are flexible to accommodate bending or compression to fit within the lumen 64 as illustrated in FIG. 5. Therefore, the material which makes up these elements is preferably sufficiently elastic to return to its expanded shape after being stored in its compressed state within the lumen 64. However, the material must also be strong enough to transfer sufficient longitudinal elongation force to the stent 10.

A number of materials can be used to form the halo 62, 66 and the spokes 63, 68 of the extraction guidewire 56, as will be recognized by one skilled in the art. For example, either of the elements may be made from metal wire, a polymeric material such as nylon or the like. In addition, the same material or different material may be used to make the halo 62, 66 and the spokes 63, 68, as long as the material chosen for each meets the above criteria. Further, it may be desirable that the material chosen be radiopaque. In one embodiment, the halo is formed from a soldered ring of stranded wire such as seven strands of 0.0005 inch diameter stainless steel wire having a total diameter of about 0.0015 inch, obtainable from Fort Wayne Metals, Fort Wayne, Ind.

Preferably, the stock of halo 62, 66 is between about 0.001 inches and 0.005 inches in diameter. A thickness less than about 0.001 inches can be used, however, the ring may not be strong enough to transfer the required force to elongate the stent 10. In addition, thicknesses greater than about 0.005 inches may be used. However, if the thickness becomes too large, undesired conditions may occur such as inadequate flexibility during the implantation or extraction procedure.

Preferably, the spokes 68 are made of spring hardness stainless steel. Spokes 68 are of sufficient length and resilience to bias the halo 66 against the interior surface of the stent such that the contact surface 58 of the halo 66 contacts the distal projections 26 of the stent 10 when the halo 66 is in the extended position. The spokes 68 can be anywhere from 0.010 inches to 0.100 inches or more in length depending on the diameter of the stent 10 and the length of the projections 26. The spokes 63, 68 are preferably between 0.020 and 0.050 inches in length for use with a typical 0.130 inch inflated diameter coronary stent 10.

Figure 6:
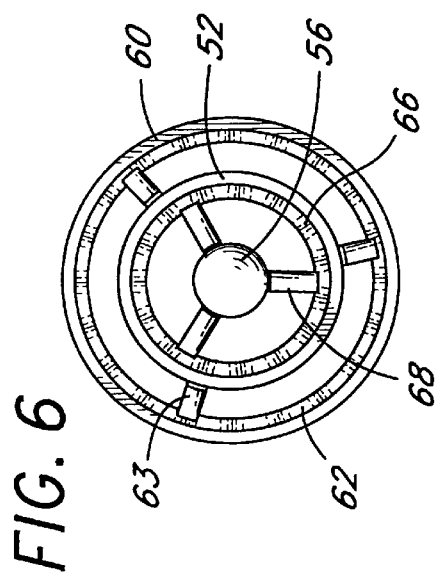
FIG. 6 is an end view taken through the line 6—6 of the extraction catheter of FIG. 5.
Figure 7:
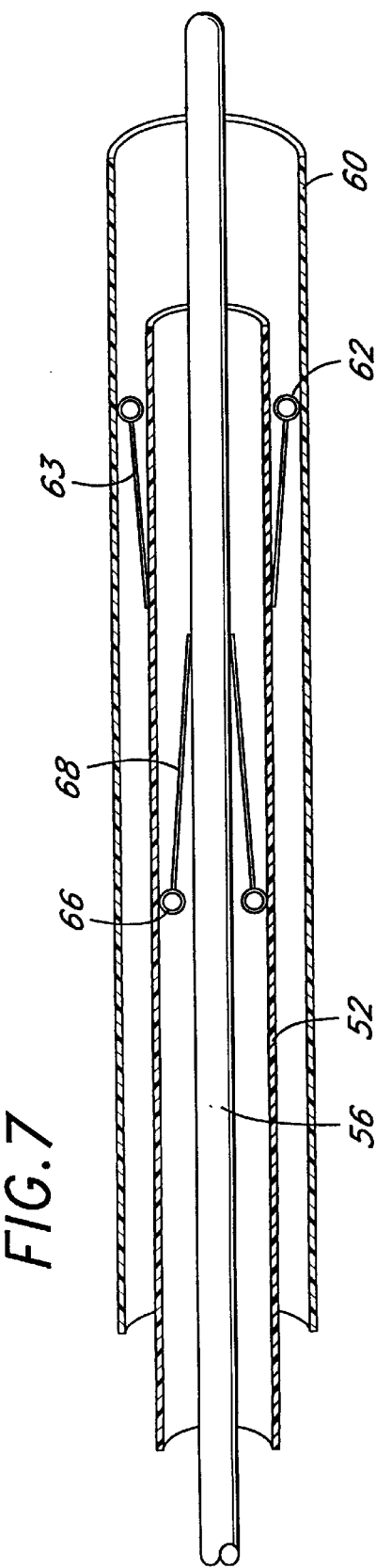
FIG. 7 is a side elevational cross sectional view of the catheter illustrated in FIG. 4, in the contracted position.

As illustrated in FIGS. 5–7, the halo 66 and spokes 68 of the guidewire 56 are bent into a radially restricted position when the guidewire 56 is positioned within the central lumen 64. The halo 66 is designed such that it can be radially compressed to be stored within the lumen 64 of the tubular body 52, and then automatically expand radially outwardly upon axial displacement beyond the distal end of central lumen 64. For example, referring to FIG. 5, each of the halos 62 and 66 can be reduced in radial diameter by bending into a sine wave configuration which will permit the diameter of both the tube 52 and the outer tube 60 to be In addition, the halos 62 and 66 can be collapsed radially inwardly with the spokes 63 and 68 inclining in either the proximal or distal direction. Referring to FIG. 7, a preferred packing arrangement is disclosed. In the illustrated embodiment, the spokes 68 on guidewire 56 are inclined in the proximal direction, while spokes 63 on inner tube 52 are inclined in a distal direction. This configuration has been determined to conveniently facilitate a radially inwardly directed force upon the application of axial stretching force on the stent, as will apparent to one of skill in the art.

As will be apparent to one of skill in the art a number of designs for the halos 62, 66 and spokes 63, 68 are possible which will provide a radial outward bias. The annular halos 62, 66 and spokes 63, 68 design should be considered as only one of a number of possible embodiments which would achieve the above described function.

Using the above described removal catheter 50, several procedures can be used to remove the stent 10 of the present invention, as will be apparent to one of skilled in the art. Some exemplary procedures that can be used are described below, however, many variations on these procedure will be possible depending on the exact stent and catheter design.

In accordance with the method of the present invention, the stent 10 is inserted into an artery 13 using a conventional balloon catheter insertion procedure. In general, a stent 10 is positioned on a deflated dilatation balloon. Preferably, a stent 10 of the type illustrated in FIG. 1 is positioned on the balloon such that an equal force will be distributed throughout the length of the stent 10 when the balloon is inflated. Depending upon stent design, the stent 10 may be gently pulled in a longitudinal direction causing the diameter of the stent 10 to contract and remain in contact with the deflated balloon.

The balloon is then navigated distally and positioned at the treatment site using procedures well known in the art. The balloon is inflated, thereby expanding the stent 10 radially outwardly until it contacts either a previously dilated, or presently stenosed wall. The balloon may be further expanded to force the stent 10 and a stenosed vascular wall 12 until it reaches a desired enlarged diameter. A balloon may be used which has two or more annular recesses to accommodate projection 26. Balloons made of PET are particularly suitable for this kind of construction.

Thus, the stent can be inserted following a dilatation, or the stent can be inserted on the dilatation balloon to simultaneously accomplish dilatation and stent implantation. If the elastic jacket of stent 10 has been impregnated with a drug, the expansion of the stent stretches the pores of the elastic jacket and commences or enhances the delivery of drugs to the treatment site on the vascular wall 12.

The balloon is thereafter deflated, and removed from the body using conventional techniques. The stent 10 remains in its expanded position due to the design of the lattice structure 20 of the stent 10.

Figure 8:
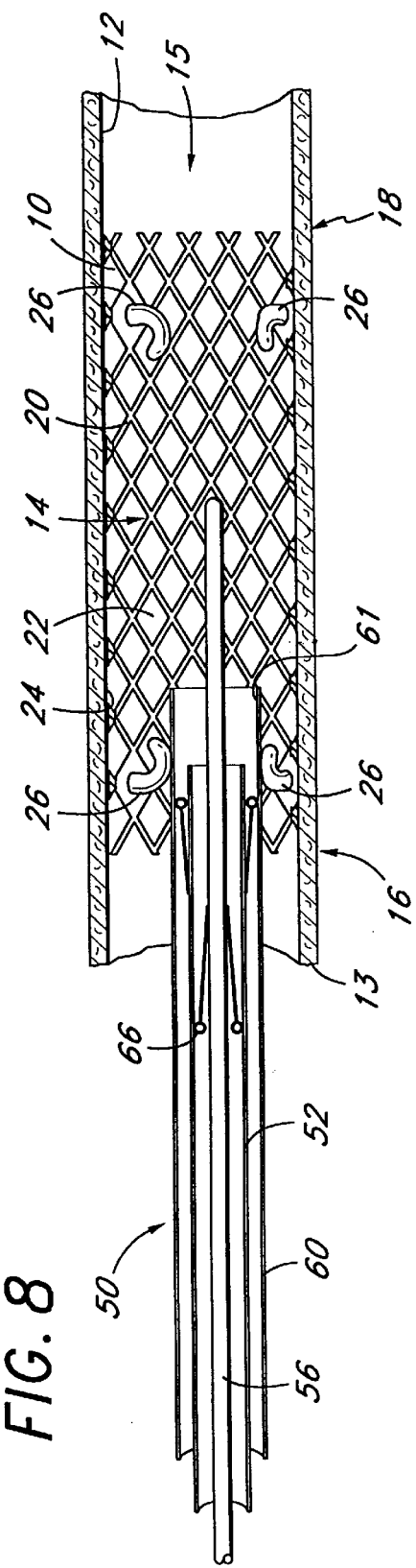
FIG. 8 is an elevational cross sectional view of the catheter of FIG. 7, positioned within an implanted stent.

An exemplary but nonexclusive procedure used to extract a stent 10 of the type illustrated in FIGS. 1–2 with an extraction catheter 50 as illustrated in FIGS. 4–7 is described below with reference to FIGS. 8–11. Referring to FIG. 8, the extraction catheter 50 is navigated to a location proximal to the stent 10 using standard angioplasty catheter advancement procedures. The distal end 61 of outer tube 60 is advanced into the lumen 15 of stent 10, and positioned between the proximal and distal sets of projections 26.

Figure 9:
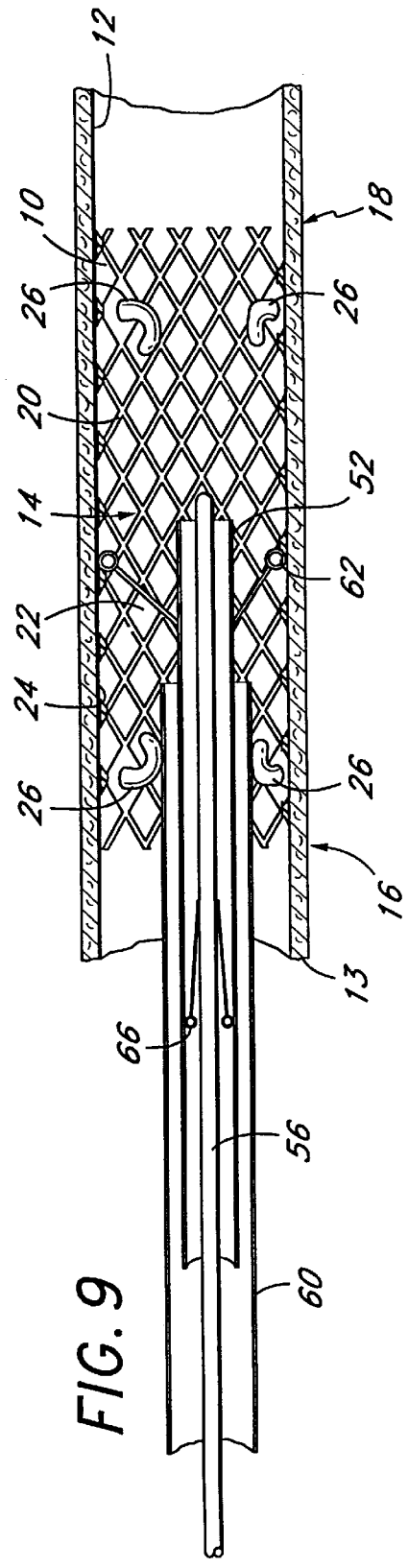
FIG. 9 is a cross sectional elevational view as in FIG. 8, with the inner tube distally extended.

Following positioning of the catheter 50 as illustrated in FIG. 8, either of the guidewire 56 or the inner tube 52 is advanced distally into the stent. Referring to FIG. 9, there is illustrated an embodiment of the method in which the inner tube 52 is advanced a sufficient distance into the stent so that the halo 62 is released from the outer tube 60. Halo 62 expands radially outwardly under the bias exerted by the halo 62 and spokes 63.

Either simultaneously or sequentially thereafter, the guidewire 56 is advanced a sufficient distance distally so that the halo 66 is released from the distal end of the inner tube 52. Halo 66 similarly expands radially outwardly to intercept the distal engagement structures on the stent 10.

Figure 10:
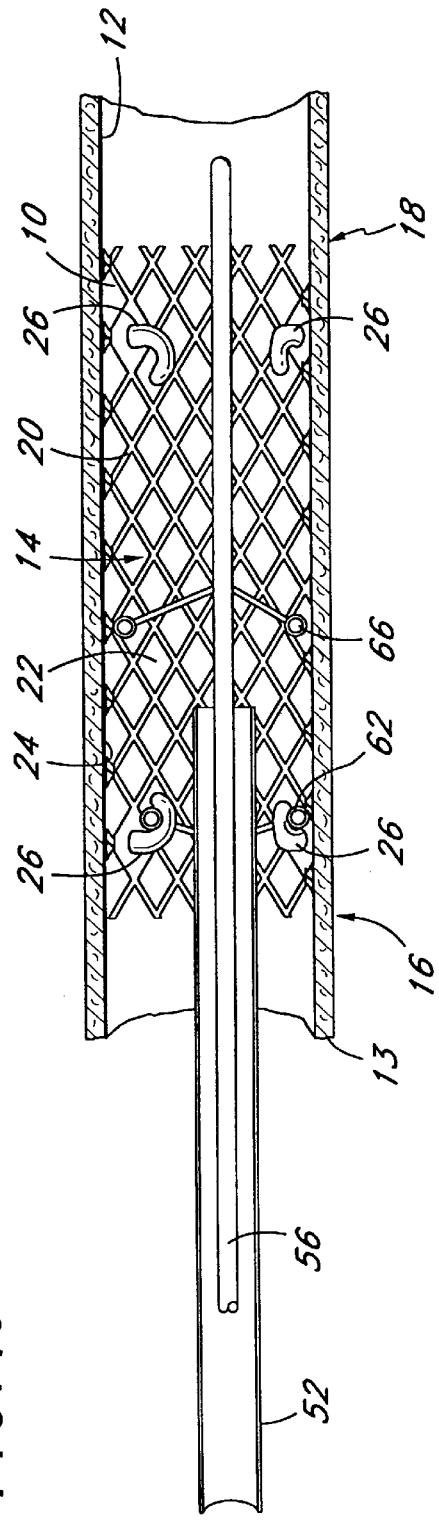
FIG. 10 is a cross sectional elevational view as in FIG. 9, with the guidewire extended.
Figure 11:
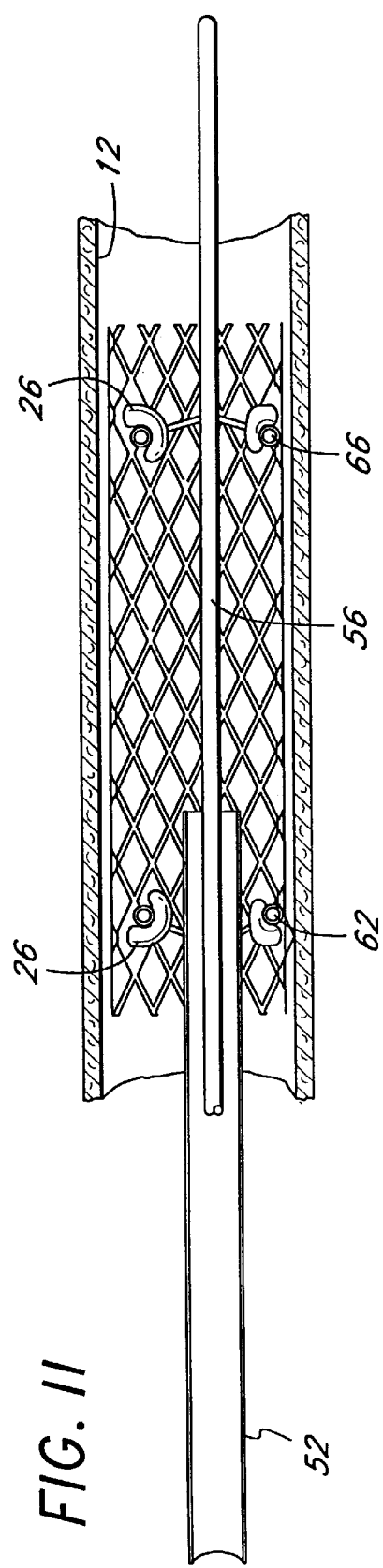
FIG. 11 is an elevational cross sectional view as in FIG. 10, with the proximal and distal engagement structures engaged, and the stent radially reduced.

The halo 62 is thereafter seated in the proximal projections 26 as illustrated in FIGS. 10 and 11, and the halo 66 is seated in the distal projections 26. The guidewire 56 is then advanced distally with respect to the inner tube 52, thereby axially elongating the tubular stent 10 and reducing its cross sectional area. See FIG. 11. As will be understood from the Figures, the very action of pulling on the spokes in the direction opposite in which they are deflected creates an inward pull on the halo, and hence the stent, aiding the contraction effect on the stent through elongation.

Axial elongation is continued until the diameter of the stent 10 is sufficiently reduced for removal from the vascular site. In one embodiment of the method of the present invention, the tubular body 52 with the stent engaged thereon is advanced into the distal end of the outer tube 60 to minimize trauma to the vascular intima during withdrawal of the catheter from the body.

A variety of modifications to the stent and structure can be made, without departing from the method of the present invention. For example, the inner tube 52 can be provided with two or more radially outwardly biased halos such as halo 62, for engaging multiple sets of projections 26 within the tubular lumen of the stent 10. This may be desirable to assist in the collapse of particularly long stents. In one modification of the present invention, a third set of projections 26 is provided midway between the proximal projections and the distal projection. A second halo 62 is provided on the inner tube 52, and spaced apart from the first halo 62, so that each of the two halos 62 on the inner tube 52 and the halo 66 on the guidewire 56 is adapted to engage a unique set projections 26 on the stent 10. In this manner, a radially inwardly directed force can be generated at a midpoint in the stent, to facilitate radial collapse.

In accordance with a further aspect of the present invention, there is provided a method for removing an implanted stent 30 of the type illustrated in FIG. 3. The removal catheter for use with the stent illustrated in FIG. 3 comprises an outer tubular body 60 as illustrated in FIG. 4, together with a guidewire 56 having an annular halo 66 thereon. The inner tube 52 and the halo 62 is not necessary for this embodiment.

The implanted stent of FIG. 3 is approached for removal from the proximal end 16 thereof. The outer tube 60 is advanced distally so that the distal end of the outer tube 60 surrounds the proximal tapered portion of the stent 30.

The guidewire 56 is thereafter advanced distally so that halo 66 travels through the opening in the proximal end 16 of the stent 30, and beyond projections 26. Distal travel of the halo 66 beyond projections 26 can be accomplished either by a resilient deflection of the halo 66 and/or projection 26, or by the use of an inner tube such as 52, however which is not provided with a halo 62.

Once the halo 66 is disposed distally of the projections 26, proximal traction on the guidewire 56 will seat the halo 66 within projections 26, and tend to pull the stent into the outer tube 60. Continued traction on the guidewire 56 with respect to the outer tube 60 will draw the stent within the outer tube 60, by a radial compression of the stent as it enters the distal opening on outer tube 60. Trauma to the vascular intima can be minimized by gradually advancing the outer tube 60 in a distal direction while maintaining traction on the guidewire 56 such that the expanded stent is not displaced axially within the artery. Once the stent has been fully drawn into the outer tube 60, outer tube 60 can be withdrawn from the body.

The removal catheter disclosed herein can also function as an insertion catheter, such as for use with self expandable stents. For example, stents formed from flexible non-metal materials such as elastomeric polymers or rubber, such as latex, are installed onto the removal catheter prior to insertion into the patient. The removal catheter is manipulated to axially elongate the tubular stent, thereby producing a radial reduction thereof. In a catheter embodiment such as that illustrated in FIG. 4, the stent may further be withdrawn within the tube 60, for positioning within the patient.

Once the stent has been positioned at the treatment site, axial elongating tension is released, and it is permitted to radially expand against the lumen wall. Thereafter, the annular halos 62, 66 or corresponding structure of the removal tool are withdrawn within the tubular body, so that they may be proximally withdrawn from within the implanted stent. For example, guidewire 56 may be proximally withdrawn into inner tube 52, and thereafter inner tube 52 is proximally withdrawn to bring halo 62 within outer tube 60. In this manner, the distal end of the removal catheter 50 can be withdrawn from the implanted stent without engaging the proximal engagement members thereof. The same stent can thereafter removed, such as in a subsequent procedure, in accordance with the methods described previously.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed is:

1. An extraction catheter for removing a stent from within a body lumen, comprising:

an elongate tubular body having at least one lumen extending axially therethrough;

a proximal engagement member on said tubular body adapted to engage a projection on a first end of a tubular flexible stent;

an axially movable support extending through said lumen; and a distal engagement member on said support adapted to engage a projection on a second end of a tubular, flexible stent, wherein said proximal engagement member is axially moveable relative to said distal engagement member such that when the proximal engagement member is moved axially away from the distal engagement member during use they are adapted to elongate a tubular, flexible stent in an axial direction sufficiently to allow for easier extraction of a stent.

2. An extraction catheter as in claim 1, wherein said axially moveable support comprises an elongate flexible guidewire.

3. An extraction catheter as in claim 1, wherein the proximal engagement member comprises a proximal contact surface for engaging the first end of the stent.

4. An extraction catheter as in claim 3, wherein the contact surface is on a annular engagement ring which surrounds the tubular body.

5. An extraction catheter as in claim 4, wherein the ring is moveable between a radially retracted position in close proximity to the tubular body and a radially extended position radially outwardly spaced from the tubular body.

6. An extraction catheter as in claim 5, further comprising one or more spokes for connecting the engagement ring to the tubular body.

7. An extraction catheter as in claim 3, wherein the proximal contact surface is biased radially outwardly from the tubular body.

8. An extraction catheter as in claim 7, wherein the distal engagement member comprises a distal contact surface which is biased radially outwardly from the tubular body.

9. An extraction catheter as in claim 8, further comprising an outer tubular sheath for maintaining the proximal and distal contact surfaces in a radially retracted position.

10. An extraction catheter of the type having engagement members on each of the proximal and distal ends thereof for use with a removable cardiovascular stent, said stent being tubular in shape and flexible in that it is configured to reduce in cross sectional area in response to axial elongation such as by axial separation of the proximal and distal engagement members, said catheter comprising:

an elongate tubular body having a proximal control end and a distal functional end, and at least one lumen extending from the proximal control end to said distal functional end;

a proximal engagement member on the tubular body adapted to releasably engage at least one projection on a proximal end of a tubular, flexible stent; and a distal engagement member axially movably disposed with respect to the tubular body and adapted to releasably engage at least one projection on a distal end of a flexible, tubular stent, wherein said distal engagement member is moveable in a distal axial direction relative to said tubular body during extraction of a stent such that it is adapted to sufficiently elongate said stent in an axial direction.

11. An extraction catheter as in claim 10, wherein said proximal engagement member comprises a flexible annular flange mounted on the tubular body.

12. An extraction catheter as in claim 11, further comprising an outer tubular sheath for maintaining said flange in a radially retracted position.

* * * * *